US00PP23007P2

(12) United States Plant Patent
Brugliera

(10) Patent No.: US PP23,007 P2
(45) Date of Patent: Sep. 4, 2012

(54) ***DIANTHUS* PLANT NAMED 'FLORIPEARL'**

(50) Latin Name: *Dianthus caryophyllus*
Varietal Denomination: Floripearl

(75) Inventor: Filippa Brugliera, Preston (AU)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/930,265

(22) Filed: Dec. 31, 2010

(51) Int. Cl.
*A01H 5/00* (2006.01)

(52) U.S. Cl. ..... Plt./273

(58) Field of Classification Search ..... Plt./273, Plt./272, 277
See application file for complete search history.

*Primary Examiner* — Kent L Bell
(74) *Attorney, Agent, or Firm* — C. A. Whealy

(57) ABSTRACT

A new and distinct cultivar of *Dianthus* plant named 'Floripearl', characterized by its upright plant habit; freely flowering habit; spray-type inflorescence form; and purple violet-colored flowers positioned upright on strong peduncles.

1 Drawing Sheet

Botanical designation: *Dianthus caryophyllus.*
Cultivar denomination: 'FLORIPEARL'.

BACKGROUND OF THE INVENTION

The present invention relates to a new and distinct cultivar of *Dianthus* plant, botanically known as *Dianthus caryophyllus*, typically grown commercially as a cut flower or as a potted plant and hereinafter referred to by the name 'Floripearl'.

The new *Dianthus* plant is a product of a planned breeding program conducted by the Inventor in Bundoora, Victoria, Australia. The objective of the breeding program was to develop new *Dianthus* plants with attractive and unique flower coloration.

The new *Dianthus* is a naturally-occurring whole plant mutation of *Dianthus caryophyllus* 'Cerise Westpearl', not patented. The new *Dianthus* plant was discovered and selected by the Inventor as a single flowering plant within a population of plants of 'Cerise Westpearl' in a controlled greenhouse environment in Bundoora, Victoria, Australia in July, 2005.

Asexual reproduction of the new *Dianthus* plant by terminal cuttings propagated in a controlled greenhouse environment in Bundoora, Victoria, Australia since February, 2007 has shown that the unique features of this new *Dianthus* plant are stable and reproduced true to type in successive generations of asexual reproduction.

SUMMARY OF THE INVENTION

Plants of the new *Dianthus* have not been observed under all possible environmental conditions. The phenotype may vary somewhat with variations in environment such as temperature and light intensity, without, however, any variance in genotype.

The following traits have been repeatedly observed and are determined to be the unique characteristics of 'Floripearl'. These characteristics in combination distinguish 'Floripearl' as a new and distinct cultivar of *Dianthus* plant:

1. Upright plant habit.
2. Freely flowering habit.

3. Spray-type inflorescence form.
4. Purple violet-colored flowers positioned upright on strong peduncles.

Plants of the new *Dianthus* differ from plants of the parent, 'Cerise Westpearl', in the following characteristics:

1. Plants of the new *Dianthus* are shorter and have shorter internodes than plants of 'Cerise Westpearl'.
2. Flowers of plants of the new *Dianthus* and 'Cerise Westpearl' differ in flower color as plants of 'Cerise Westpearl' have red purple-colored flowers.

Plants of the new *Dianthus* can be compared to plants of the *Dianthus* 'Florijade', disclosed in U.S. Plant Pat. No. 21,515. In side-by-side comparisons conducted in Bundoora, Victoria, Australia, plants of the new *Dianthus* differed from plants of 'Florijade' in the following characteristics:

1. Plants of the new *Dianthus* had shorter internodes than plants of 'Florijade'.
2. Flowers of plants of the new *Dianthus* had more petals than flowers of plants of 'Florijade'.
3. Plants of the new *Dianthus* had longer peduncles than plants of 'Florijade'.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph at the top of the sheet comprises a side perspective view of a typical plant of 'Floripearl' grown in a container.

The photograph at the bottom of the sheet is a close-up view of a typical leaf, flower bud, opened flower and petals of 'Floripearl'.

DETAILED BOTANICAL DESCRIPTION

Plants used in the aforementioned photographs and following observations and measurements describe plants grown during the winter in 22-cm containers in a polycarbonate-covered greenhouse in Bundoora, Victoria, Australia and under conditions and practices which approximate those generally used in commercial *Dianthus* production. During the production of the plants, day temperatures averaged 21° C., night temperatures averaged 18° C. and light levels averaged 1.19 kilolux. Plants were 26 weeks old when the photographs and the detailed description were taken. In the following description, color references are made to The Royal Horticultural Society Colour Chart, 2007 Edition, except where general terms of ordinary dictionary significance are used.

Botanical classification: *Dianthus caryophyllus* 'Floripearl'.

Parentage: Naturally-occurring whole plant mutation of *Dianthus caryophyllus* 'Cerise Westpearl', not patented.

Propagation:

*Type*.—By terminal cuttings.

*Time to produce a rooted young plant*.—About three to four weeks at soil temperatures of 18° C. to 22° C.

*Root description*.—Fine, fibrous; creamy white in color.

*Rooting habit*.—Moderate branching; medium density.

Plant description:

*Plant form*.—Upright plant habit; narrow inverted triangle; spray-type inflorescence form; axillary branching; strong stems.

*Plant height*.—About 92 cm.

*Plant diameter or spread*.—About 15 cm to 18 cm.

*Lateral branches*.—Length: About 81 cm. Diameter: About 8 mm. Internode length: About 6.5 mm. Node length: About 4 mm. Node diameter: About 6 mm. Texture: Glabrous, glaucous. Color: Close to 137B; at the nodes, close to 192A.

Foliage description:

*Arrangement*.—Opposite, simple; sessile.

*Length*.—About 4.8 cm.

*Width*.—About 6 mm.

*Shape*.—Lanceolate.

*Apex*.—Acute.

*Base*.—Decurrent, sheathing.

*Margin*.—Entire.

*Texture, upper and lower surfaces*.—Glabrous, glaucous.

*Venation pattern*.—Parallel.

*Color*.—Developing leaves, upper and lower surfaces: Close to 138A. Fully expanded leaves, upper and lower surfaces: Close to 138A; venation, close to 138A.

Flower description:

*Flower type and habit*.—Large double flowers; flowers terminal and axillary in cymose sprays; freely flowering habit with numerous flowers developing per plant; flowers positioned on strong peduncles; flowers face mostly upright.

*Fragrance*.—None detected.

*Natural flowering season*.—Flowering is continuous through the summer and late summer in Australia; plants begin flowering about 170 days after planting.

*Flower longevity*.—Flowers last about 18 days on the plant; flowers persistent.

*Flower buds*.—Length: About 2.9 cm. Diameter: About 1 cm. Shape: Cylindrical. Color: Close to 138A.

*Corolla*.—Quantity of petals/arrangement: About 42 per flower arranged in several whorls; imbricate. Corolla height: About 2.6 cm. Petal length: About 4.9 cm. Petal width: About 2.4 cm. Petal shape: Roughly obdeltoid. Petal apex: Praemorse. Petal base: Acute. Petal margin: Crenate to entire. Petal texture, upper and lower surfaces: Smooth, glabrous. Petal color: When opening, upper and lower surfaces: Close to N82B; towards the base, close to 145D. Fully opened, upper and lower surfaces: Close to N82B; towards the base, close to 145D.

*Calyx*.—Quantity of sepals/arrangement: Six in a single whorl. Calyx height: About 2.8 cm. Calyx diameter, at the apex: About 1.6 cm. Sepal texture, upper and lower surfaces: Smooth, glabrous. Sepal color, upper and lower surfaces: Close to 143A.

*Peduncles*.—Length: About 4 cm. Diameter: About 2 mm. Strength: Strong. Texture: Glabrous, glaucous. Color: Close to 138A.

*Reproductive organs*.—Stamens: Quantity: About nine per flower; anthers dorsifixed. Filament length: About 1.6 cm. Filament color: Close to NN155B. Anther length: About 2.7 mm. Anther diameter: About 1 mm. Anther color: Close to 156D. Pollen amount: Scarce. Pistils: Quantity: One, bi-parted. Pistil length: About 3.2 cm. Style length: About 1.8 mm. Style color: Close to 155A. Stigma shape: Club-shaped. Stigma color: Close to 155A. Ovary size: About 7 mm by 5 mm. Ovary shape: Obovoid. Ovary color: Towards the apex, close to 145A; towards the base, close to 155A.

*Fruits/seeds*.—Fruit and seed development have not been observed on plants of the new *Dianthus*.

Disease/pest resistance: Plants of the new *Dianthus* have not been observed to be resistant to pathogens and pests common to *Dianthus* plants.

Temperature tolerance: Plants of the new *Dianthus* have been observed to tolerate temperatures ranging from about −2° C. to about 40° C.

It is claimed:

1. A new and distinct *Dianthus* plant named 'Floripearl' as illustrated and described.

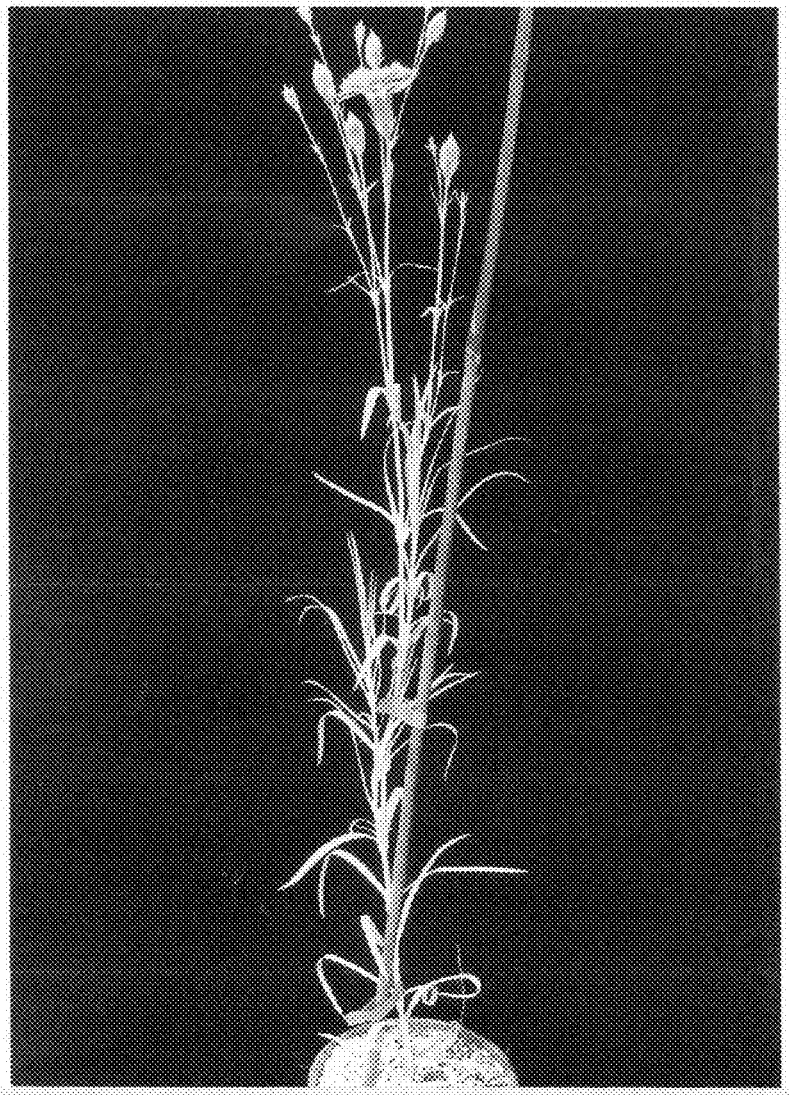
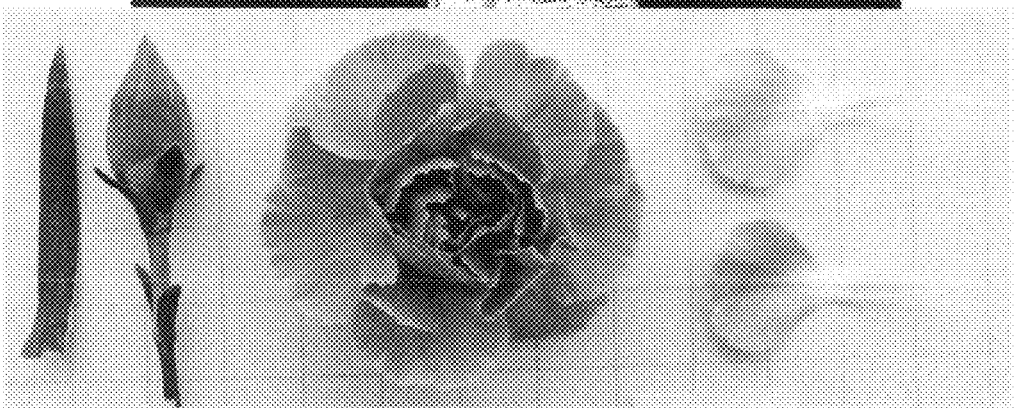

* * * * *